United States Patent [19]

Grundei

[11] Patent Number: 5,672,149
[45] Date of Patent: Sep. 30, 1997

[54] CLAVICLE BANDAGE

[75] Inventor: Hans Grundei, Lübeck, Germany

[73] Assignee: Schütt & Grundei Orthopadietechnik GmbH, Lübeck, Germany

[21] Appl. No.: 603,532

[22] Filed: Feb. 21, 1996

[30] Foreign Application Priority Data

Feb. 21, 1995 [DE] Germany .................. 195 05 854.2

[51] Int. Cl.$^6$ ........................................ A61F 5/01
[52] U.S. Cl. ........................... 602/19; 128/DIG. 19
[58] Field of Search .................. 128/DIG. 19; 602/4–5, 602/19–20, 60–61

[56] References Cited

U.S. PATENT DOCUMENTS

| | | | |
|---|---|---|---|
| 496,816 | 5/1893 | Corker | 602/19 |
| 1,755,641 | 4/1930 | Foulke | 602/19 |
| 3,141,456 | 7/1964 | Meek | 602/19 |
| 3,382,868 | 5/1968 | Stiefel . | |
| 3,718,137 | 2/1973 | Gaylord, Jr. | 602/19 |
| 3,897,776 | 8/1975 | Gaylord, Jr. | 602/19 |
| 4,589,406 | 5/1986 | Florek | 602/19 |
| 4,930,499 | 6/1990 | Rowe | 602/19 |
| 5,074,292 | 12/1991 | Cox . | |
| 5,127,897 | 7/1992 | Roller | 602/19 |
| 5,489,260 | 2/1996 | Striano | 602/19 |

FOREIGN PATENT DOCUMENTS 223577  10/1925  United Kingdom .

*Primary Examiner*—Richard J. Apley
*Assistant Examiner*—David R. Risley
*Attorney, Agent, or Firm*—Panitch Schwarze Jacobs & Nadel, PC.

[57] ABSTRACT

A clavicle orthotic device has two bands (8, 8') of essentially non-elastic material adjustable in length. The bands (8, 8') are permanently attached at their respective first ends (3, 3') to a common support element (2) and can be detachably fastened to the support element at their respective second ends (4, 4'). For increasing wearing comfort through the greatest freedom of movement possible with simultaneous introduction of sufficient traction to the fractured clavicle, the support element (2) is constructed as an oblong plate element, at whose upper region the first ends (3, 3') are installed, and at whose lower region the second ends (4, 4') of the bands can be mounted by means of two buckles (5, 5'), whereby both buckles are positioned on the support element (2) as to be pivotable about a rotation point (6).

9 Claims, 2 Drawing Sheets

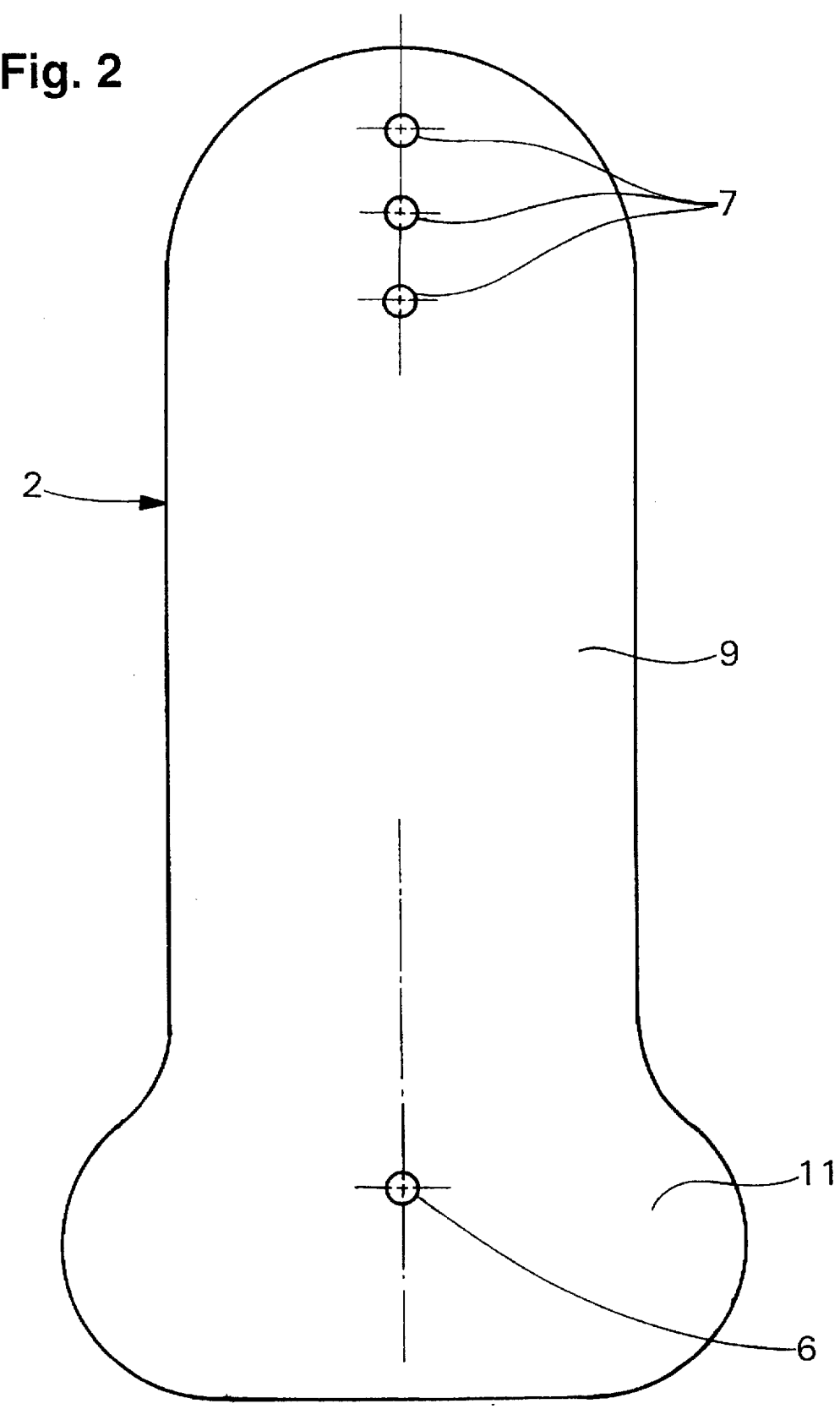

CLAVICLE BANDAGE

FIELD OF THE INVENTION

The invention concerns a clavicle bandage having two bands adjustable in length and made of essentially non-elastic material, the bands being permanently fastened at their respective first ends to a common support or holding element and detachably fastened to the support element at their respective second ends.

BACKGROUND OF THE INVENTION

Clavicle bandages of this type are known, for example, from U.S. Pat. No. 3,382,868. Such bandages serve for treatment of a fracture of the clavicle (collar bone). It is thereby a preeminent goal to immobilize the clavicle so that the fracture points move as little as possible in relation to one another during the healing phase. Naturally, a further aspect in connection with bandages of this type is that wearing comfort be as high as possible.

In connection with the known clavicle bandage of the type defined by the above patent the support element consists of an oblong strip of fabric, to which the two bands are fastened in the lower region with their second ends independent of each other, and indeed by means of a respective hook which grips into a ring attached to the support element. A certain ability of the lower ends to swivel is thereby attained, and to be sure around the middle point of the ring. This permits an adaption of the clavicle bandage in connection with movements of the shoulder blades within certain limits. Pressing of the lower end regions of the bands on the lower area of the shoulder blade cannot of course be precluded, however, which negatively affects wearing comfort and thereby the acceptance of this bandage.

A further clavicle bandage is known from EP-A-0 379 929 wherein, in contrast to the typical clavicle bandage, the support element consists of a ring to which the two bands are again fastened with their second ends independent of each other, whereby it is important that the bands are attached to each other through this ring such that the angle can be shifted. This ability to shift the angle should be simple to apply in connection with a high treatment safety, i.e., with an anatomically good fit without sliding and loosening, and pleasant for the patient to wear, as well as easy to adjust.

Through the fact that both bands begin almost in a punctiform manner on the ring which comes to lie on the back of the patient and end there again after successful application, namely the clasps which are found on the respective other ends of the bands are fastened to the ring, this part of the back is exposed to relatively high stress, i.e., traction, and as a consequence of this, to a high pressure which reduces wearing comfort, contrary to statements made in the aforementioned publication. In addition, the natural course of movement is not optimally supported by this known clavicle bandage.

Finally, reference is made furthermore to U.S. Pat. No. 5,074,292 from which, among other things, an application of a relatively large truss pad is known as part of a clavicle bandage. This truss pad covers entire parts of the back of a patient and consequently also the mobile shoulder blades. The wearing comfort of this clavicle bandage thus in no way satisfies the expectations of the patient.

SUMMARY OF THE INVENTION

Against this background, an object of the present invention is to improve the clavicle bandage of the type mentioned at the outset such that, on the one hand, the greatest possible freedom of movement for the patient possible is preserved while, on the other hand, the fractured clavicle is at the same time brought under traction with the most effective immobilization of the fracture site possible. In addition, the clavicle bandage should be subject to adjustment for the individual patient with a view toward a successful treatment.

These objects are achieved in accordance with the invention in which the support element has a perforated strip by means of which the two first ends are fixed on the support element with attachment means adjustable in height, and the support element is constructed as an essentially T-shaped oblong plate element, whereby the long leg of the T runs in the direction from caudal toward cranial region of the patient.

The firmly fixed ends of the two bands can then be adjusted for the individual patient in the respective orthopedic workshop to the effective length of the support element. Various patient body sizes can thereby be taken into consideration, if the clavicle bandage is manufactured only in one size as a standard part. The ends of the bands can be permanently fastened in the respective holes by means of rivets, for example.

By constructing the support element as an oblong plate element, a certain "backpack effect" is achieved, as before in the case of the above-described type-defining patent. In contrast with the clavicle bandage of this type, however, the support element is constructed in the shape of a T, as mentioned. The cross arm of the T-shaped support element lies below the shoulder blades on the back of the patient. The special configuration of the support element makes it possible for the patient, for example, to move his arms while walking, whereby this movement acts through the shoulder blades to the back middle to lower region of the back, without this movement exerting a disturbing action on the support element. The greatest possible wearing comfort of a clavicle bandage is obtained in this way.

In accordance with a preferred embodiment, the two permanently fixed ends of the respective bands project from the support element such that an upward projection of the main axis of the support element forms with the bands an angle in the range of 40°–50°. This configuration produces an anatomically correct introduction of tractive forces to the patient's body, while on the other hand also permitting the clavicle fracture, which mostly occurs somewhere in the middle of the clavicle, to remain free from impairments by the bands.

For reasons of symmetry, the fixation points of the first, permanently fixed ends of the bands and the pivot point of both buckles for the second ends of the bands lie preferably on the main axis of the support element. A broad symmetry of forces is obtained thereby, assuming equal band tension.

Finally, the support element is preferably made of tough bendable plastic material which is pleasant to wear, that is a plastic material which is firm or stable, yet flexible. Examples of preferred plastics for the support element include high density polyethylene, polyurethane or polyacetal. Further features can be realized in concrete specific embodiments. For example, the bands should be made of a breathable material, such as perhaps cotton, etc.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there are shown in the drawings an embodiment which is presently preferred. It should be understood, however, that the invention is not limited to the precise arrangements and instrumentalities shown. In the drawings:

FIG. 2 is an enlarged representation of the support element of the clavicle bandage.

DETAILED DESCRIPTION OF PREFERRED EMBODIMENT

Figure 1:
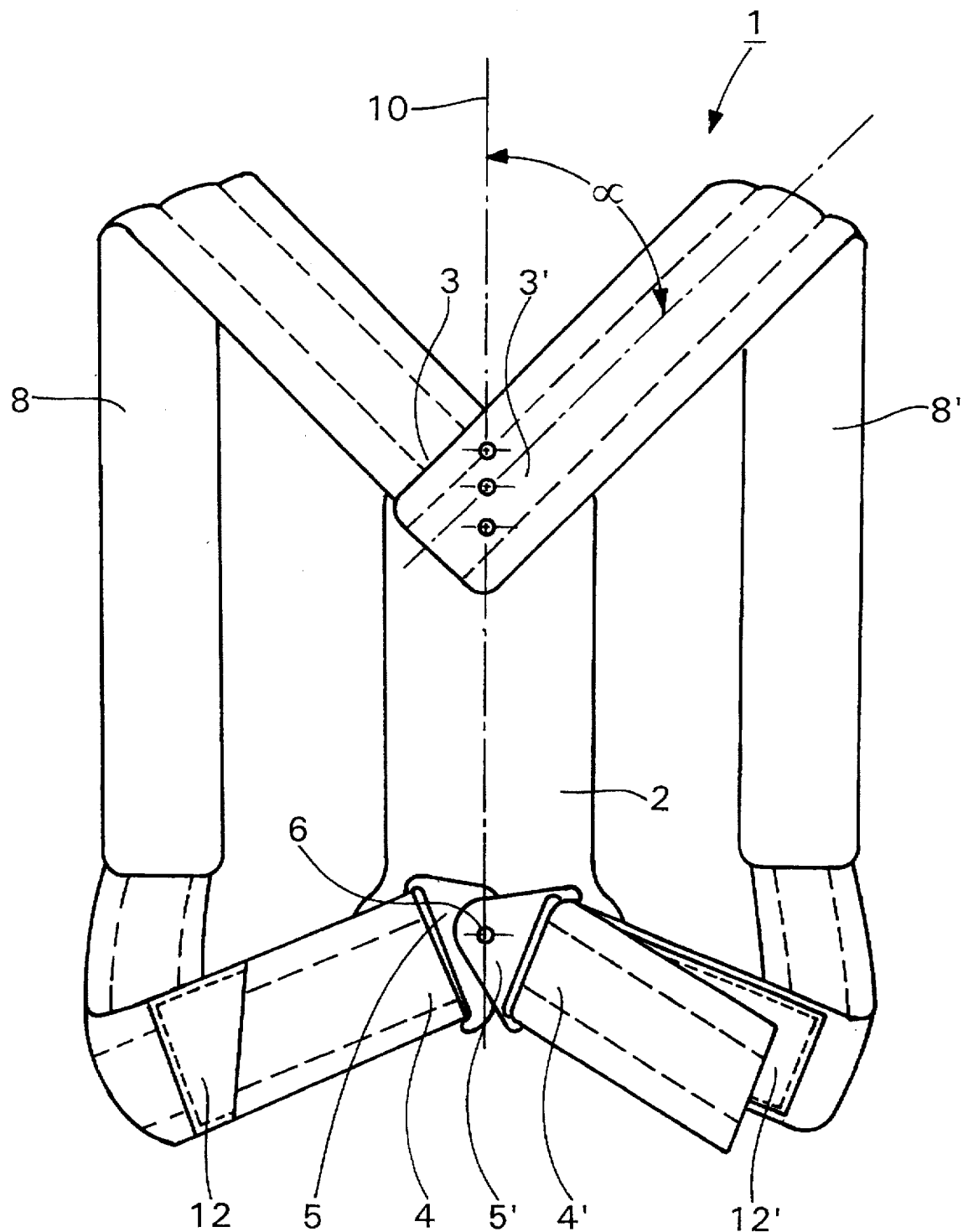
FIG. 1 is a rear view of a clavicle bandage according to the invention.

The two bands 8 and 8' of the clavicle bandage 1 are clearly recognizable in FIG. 1. The bands have in each case a first end 3 or 3' and a second end 4 or 3' The first ends 3 and 3' are permanently attached in the upper region of the support element 2, which is constructed as an oblong plate element, for example with rivets (not shown) which pass through several (at least two and preferably three or more) holes of the perforated strip 7 (FIG. 2). This permits adjusting the clavicle bandage in the orthopedic workshop according to the individual patient, i.e., the effective length of the support element is established by proper selection of the holes through which the rivets are inserted.

Depicted here furthermore is also the angle α between the respective bands 8, 8' and the main axis 10 of the clavicle bandage, which lies preferably in the range between 40°–50°.

The support element 2 is constructed as a T-shaped part, whose long leg 9 (FIG. 2) extends upwardly, thus coming to lie above the vertebral column at the back and running in the direction from caudal toward cranial region of the patient.

A pivot point 6 in the form of a boring is provided approximately at the intersection of the main axis 10 of the support element 2 with the axis of its cross arm 11. Two buckles 5 and 5' are pivotably hinged at this pivot point, by a rivet for example. The buckles 5 and 5' serve to take up the second ends 4 and 4' of the respective bands 8 and 8'. The ends 4 and 4' are passed through the buckles and fastened to the buckles 5 and 5' with Velcro locks 12 and 12', for example.

During walking the clavicle bandage 1 adapts to the movement process through the associated movement of the shoulder blades, since namely the buckles 5 and 5' experience a certain synkinesis by swivelling about the pivot point 6, without, however, impairing the immobilization of the clavicle through this. An essentially increased wearing comfort is the consequence, which furthermore promotes patient acceptance, and this can once again lead further to a better treatment success.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

I claim:

1. A clavicle orthotic device comprising an oblong support element (2), two bands (8, 8') which are adjustable in length and made of an essentially non-elastic material, the bands being attached at their respective first ends (3, 3') in an upper region of the support element (2), and being detachably fastened at their respective second ends (4, 4') in a lower region of the support element (2), and two buckles (5, 5') pivotally attached to the support element for pivotably fastening the second ends about a pivot point (6) on the support element, the support element (2) having a plurality of holes (7) in its upper region, the first ends (3, 3') of the bands being fastened with attachment means that are adjustable in height to at least one of the plurality of holes on the support element (2), and the support element (2) being constructed as an oblong plate element made of a firm, flexible material having an essentially T-shape, whereby a long leg (9) of the T-shape will run in a direction from caudal toward cranial region of a patient who wears the clavicle orthotic device.

2. The clavicle orthotic device according to claim 1, wherein the respective first ends (3, 3') of the two bands (8, 8') project from the support element (2) such that an upward projection of a main axis (10) of the support element (2) forms a respective angle α with the bands (8, 8') in a range of 40°<α<50°.

3. The clavicle orthotic device according to claim 1, wherein the hoes (7) and the pivot point (6) of the two buckles (5, 5') lie on a main axis (10) of the support element (2).

4. The clavicle orthotic device according to claim 1, wherein the support element (2) is made of a tough bendable polymeric material.

5. The clavicle orthotic device according to claim 2, wherein the support element (2) is made of a tough bendable polymeric material.

6. The clavicle orthotic device according to claim 3, wherein the support element (2) is made of a tough bendable polymeric material.

7. The clavicle orthotic device according to claim 3, wherein the pivot point (6) lies approximately at the intersection of the main axis (10) and a longitudinal axis of a cross arm (11) of the T shape.

8. The clavicle orthotic device according to claim 1, wherein there are at least two holes in the upper region of the support element and the first ends of the bands are attached to the at least two holes.

9. The clavicle orthotic device according to claim 8, wherein each of the first ends (3,3') have at least two holes for fixing to the support element (2).

* * * * *